United States Patent [19]

Koerner, Jr.

[11] Patent Number: 5,147,776
[45] Date of Patent: Sep. 15, 1992

[54] USE OF 2,5-ANHYDROMANNITOL FOR CONTROL OF PH DURING BLOOD STORAGE

[75] Inventor: Theodore A. W. Koerner, Jr., Iowa City, Iowa

[73] Assignee: University of Iowa Research Foundation, Iowa City, Iowa

[21] Appl. No.: 484,792

[22] Filed: Feb. 26, 1990

[51] Int. Cl.$^5$ ............................................. A01N 1/02
[52] U.S. Cl. ........................................ 435/2; 424/532
[58] Field of Search ............................. 424/532; 435/2

[56] References Cited

U.S. PATENT DOCUMENTS

| | | | |
|---|---|---|---|
| Re. 32,874 | 2/1989 | Rock et al. | 424/101 |
| 2,786,014 | 3/1957 | Tullis | 167/78 |
| 3,703,438 | 11/1972 | Kovgalev et al. | 195/1.8 |
| 4,082,509 | 4/1978 | Talcott | 21/58 |
| 4,344,936 | 8/1982 | Soslau | 424/101 |
| 4,356,172 | 10/1982 | Nakao et al. | 424/101 |
| 4,476,221 | 10/1984 | Kane et al. | 435/2 |
| 4,585,735 | 4/1986 | Meryman et al. | 435/2 |
| 4,670,013 | 6/1987 | Barnes et al. | 604/403 |
| 4,769,318 | 9/1988 | Hamasaki et al. | 435/2 |
| 4,812,310 | 3/1989 | Sato et al. | 424/101 |
| 4,828,976 | 5/1989 | Murphy | 435/2 |

OTHER PUBLICATIONS

Kilkson, H., Holme, S. and Murphy, S., "Platelet Metabolism During Storage of Platelet Concentrates at 22° C.," *Blood*, vol. 64, No. 2, Aug. 1984, pp. 406–414.

Slichter, Sherrill J., "In Vitri Measurements of Platelet Concentrates Stored at 4° and 22° C.: Correlation with Posttransfusion Platelet Viability and Function," *Vox Sang*, 40: suppl. 1, pp. 72–86 (1981).

Murphy, Scott, "Platelet Storage for Transfusion," *Seminars in Hematology*, vol. 23, No. 3, Jul. 1985, pp. 165–177.

Murphy, Scott, et al., "Improved Storage of Platelents for Transfusion in a New Container," *Blood*, vol. 60, No. 1 (Jul. 1982) pp. 194–200.

Riquelme, Patricio T., "Mechanism of Action of 2,5-Anhydro-D-mannitol in Hepatocytes," *The Journal of Biological Chemistry*, vol. 259, No. 8, Apr. 25, 1984, pp. 5115–5123.

Wallvik, J. et al. Vox. Sang. 45:303–311 (1983) Platelet Concentrates Stored at 22° C. Need Oxygen.

Holme, S. et al. Vox. Sang. 53:214–220 (1987) Platelet Storage Lesion in Second-Generation Containers.

Solbert, C. et al. Vox Sang. 55:97–103 (1988) Effect of Centrifugation on the Storage Properties of Platelets.

Espersen, G. et al. Vox Sang. 55:218–221 (1988) Irradiated Blood Platelet Concentrates Stored.

*Primary Examiner*—David M. Naff
*Assistant Examiner*—S. Saucier
*Attorney, Agent, or Firm*—Zarley, McKee, Thomte, Voorhees & Sease

[57] ABSTRACT

2,5-anhydro-D-mannitol is added to blood platelet storage containers at a sufficient level to maintain pH stability of blood platelets within the suitable range (pH 7.2 to 7.4) for use in blood transfusions.

9 Claims, 2 Drawing Sheets

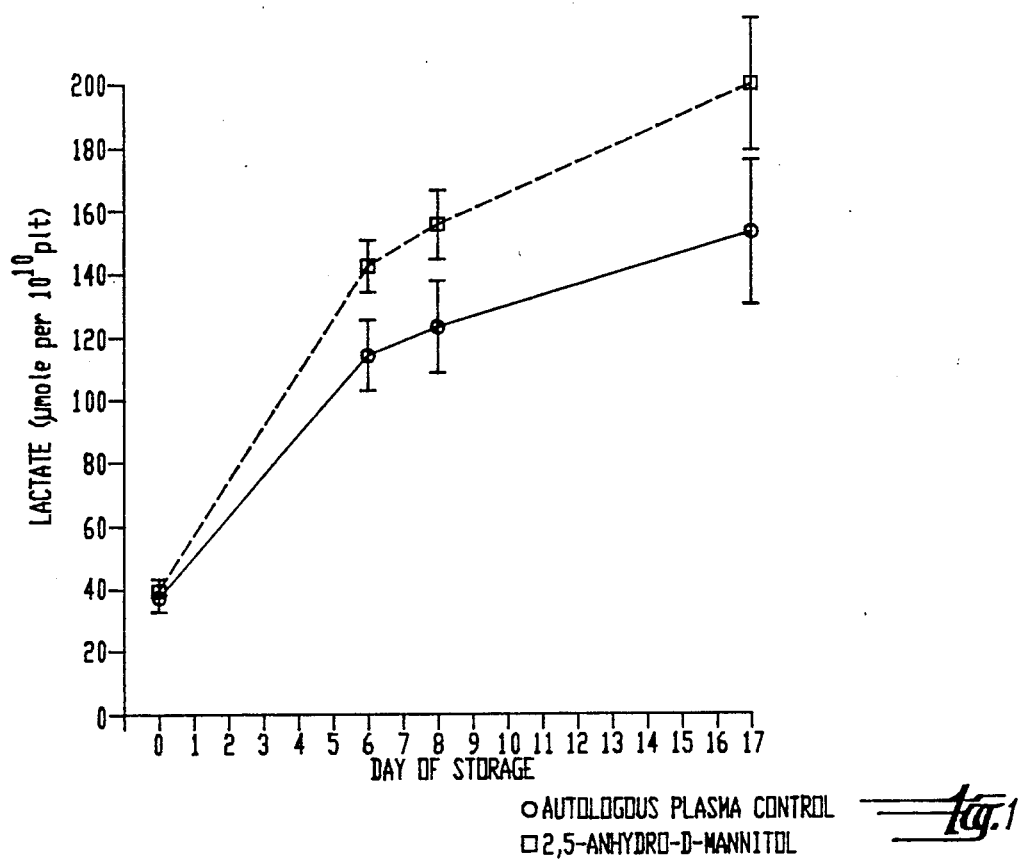
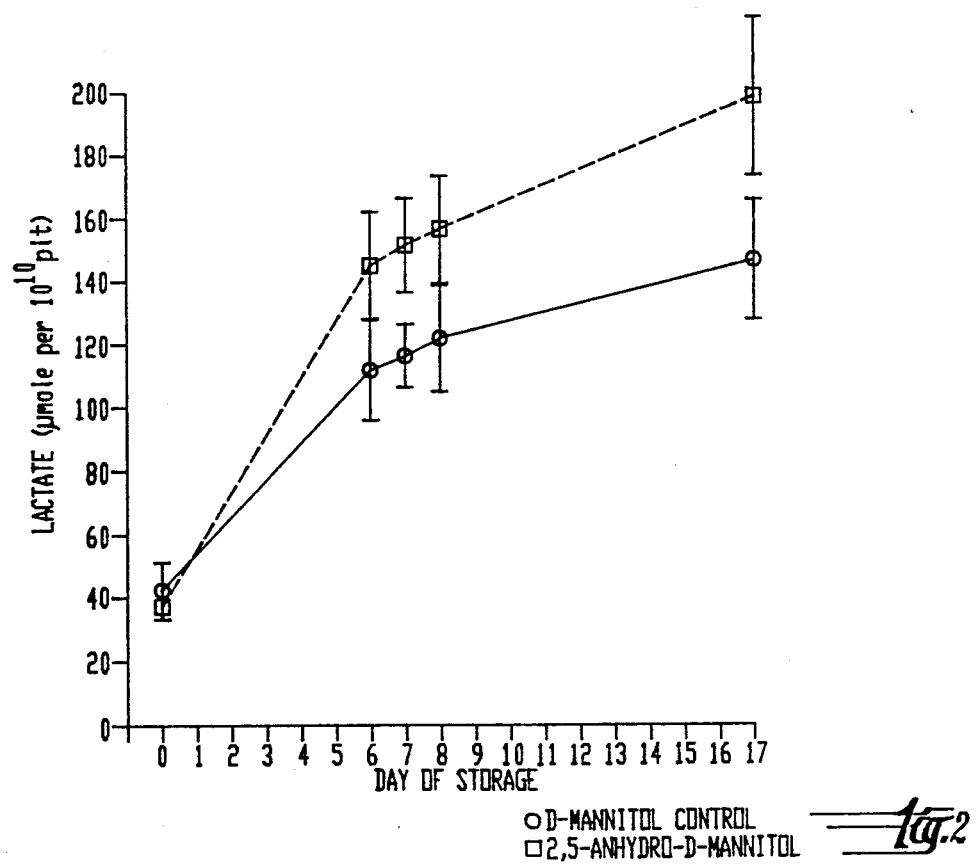

USE OF 2,5-ANHYDROMANNITOL FOR CONTROL OF PH DURING BLOOD STORAGE

BACKGROUND OF THE INVENTION

The survival and function of transfused platelets is very sensitive to storage pH. The first generation of plastic blood storage containers were made of polyvinylchloride which inhibited gas exchange with the atmosphere. This tended to cause acidic conditions (pH less than 6). Investigations revealed that these bags became acidic due to the entrapment of carbon dioxide in the bags while lactic acid accumulated from anaerobic metabolic processes occurring within the stored platelets. This gradual decrease of pH due to the presence of increasing amounts of lactic acid and entrapped carbon dioxide caused damage to the platelets, more specifically to the membrane of the cells. As a result, the transfused platelets were hemostatically ineffective and were rejected by the body of the recipient very shortly after transfusion.

This storage problem led to the development of second generation storage containers made of more gas permeable polyolefin materials. Examples of the so-called second generation storage containers are those made by Baxter-Travenol, Fenwal, and Cutter. These second generation storage containers as now available are commonly polymerized alpha olefins such as polyethylene, etc. Because they have the advantage of being gas permeable, there is the expectation that carbon dioxide can be released in compensation for the amount of lactic acid production of the stored platelets. Thus the pH will not fall. While these bags work for their intended purpose, they create an additional problem. Namely, over compensation of carbon dioxide release. Thus, the bags give up carbon dioxide so rapidly that in fact alkaline environmental conditions are induced within the storage bags. Alkaline conditions (greater than 7.5) are as damaging to platelets as acid pH. In particular, alkaline pH leads to a dramatic drop off in survival after transfusion caused by modification of the platelet membrane. This is probably due to the coating of transfused platelets with antibody and their destruction in the patient's spleen.

In short, the solving of the problem of acidic conditions created by bags which inhibit gas exchange creates the problem of too much gas exchange which tends to alkaline conditions that are just as damaging to platelets.

Accordingly, it is an object of the present invention to provide a non-toxic, non-harmful additive for use with blood storage containers which avoids both extremes of pH and instead provides a pH stable stored blood product.

Another object of the present invention is to provide a method of controlling pH of stored blood platelets.

A further object of the present invention is to provide a method of modulating lactic acid production of stored platelets by using non-toxic additives, with the result being high survival rate of stored platelets ready for use with transfused patients.

A further objective of the present invention is to employ a lactic acid stimulator to modulate lactic acid production of stored platelets which is 2,5-anhydro-D-mannitol or a nontoxic, non-harmful, derivative thereof.

The method and manner of accomplishing each of the above objectives of the present invention will become apparent from the detailed description which follows hereinafter.

SUMMARY OF THE INVENTION

Blood platelets are pH stabilized by modulation of lactic acid production of stored platelets by adding as a non-toxic, non-harmful stabilizer, 2,5-anhydro-D-mannitol or a derivative thereof.

BRIEF DESCRIPTION OF THE DRAWINGS

FIG. 1 is a graph that shows the effect of 2,5-anhydro-D-mannitol on the lactic acid production of platelet concentrate compared to a sham treatment control the graph is a plot of the number of days of storage versus micromoles of lactate produced per 10 to the tenth platelets.

FIG. 2 is a graph that shows the effect of 2,5-anhydro-D-mannitol on the lactic acid production of platelet concentrate as compared to a D-mannitol control the graph is a plot of the number of days of storage versus micromoles of lactate produced per 10 to the tenth platelets.

DETAILED DESCRIPTION OF THE INVENTION

Figure 3:
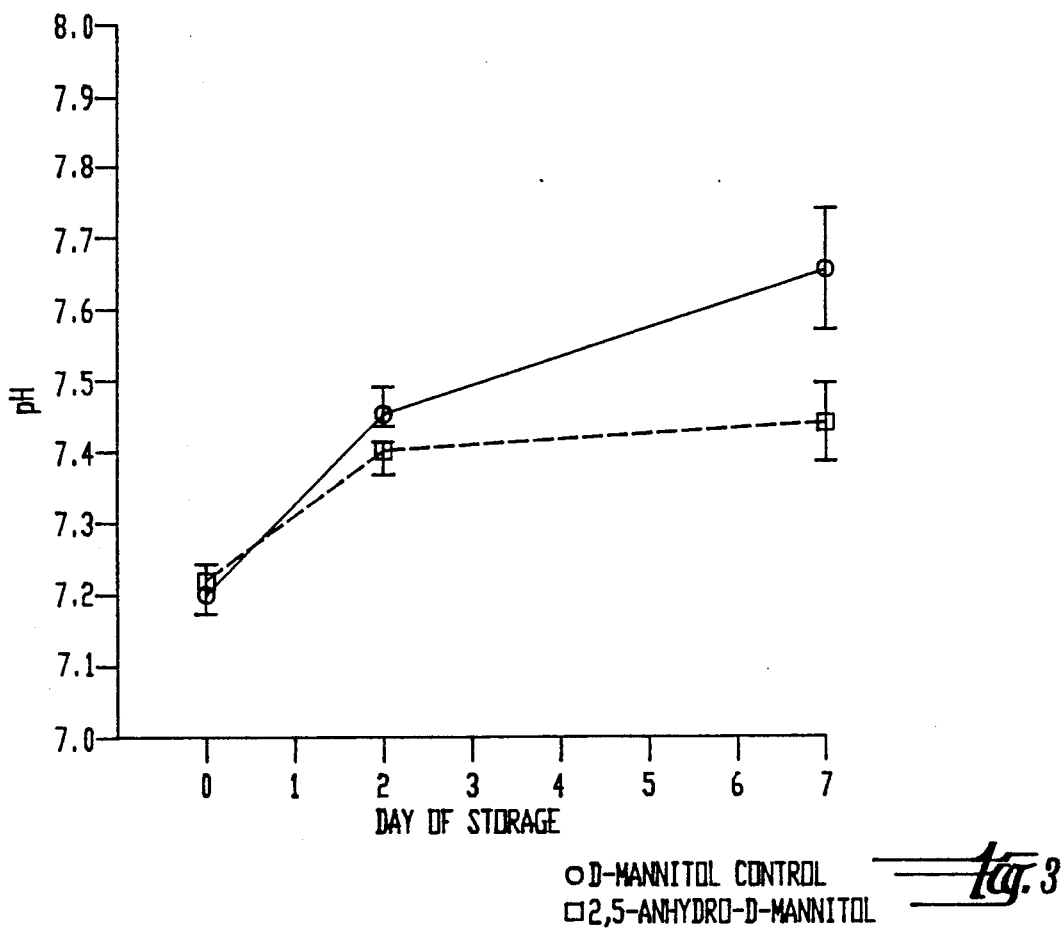
FIG. 3 is a graph that shows the effect of 2,5-anhydro-D-mannitol on the pH of platelet concentrate compared to a D-mannitol control the graph is a plot of the number of days of storage versus the pH of the platelet concentrate.

The addition of D-mannitol itself as an additive to storage solutions for preserving functional cells such as platelets is known, see Kane, et al., U.S. Pat. No. 4,476,221, issued Oct. 9, 1984. However, as demonstrated herein in the examples below, mannitol does not work as a storage additive for stabilizing the pH of blood platelets in blood bags. It is therefore surprising and unexpected that 2,5-anhydro-D-mannitol, which is a derivative of the sugar alcohol D-mannitol, does work. 2,5-anhydro-D-mannitol is formed by the heat catalyzed dehydration across the C-2 and C-5 hydroxyl groups of D-mannitol and formation of an internal ether. 2,5-anhydro-D-mannitol is non-toxic, having an intraperitoneal $LD_{50}$ in mice approximately equal to D-glucose. Extensive biochemical studies over the last fifteen years have shown 2,5-anhydro-D-mannitol to be slowly taken up by mammalian cells, and due to its structural resemblance to D-fructofuranose, to become phosphorylated. The resulting 2,5-anhydro-D-mannitol-1,6-bisphosphate then inhibits the enzyme fructose 1,6-bisphosphatase and activates the enzyme pyruvate kinase. The combination of these effects inhibits gluconeogenesis and stimulates lactic acid formation.

In a predominantly glycolytic cell like the platelet these effects have been found to act as a "tonic" to stimulate anaerobic metabolism and lactic acid production. The resulting lactic acid, if formed gradually over the storage period, counteracts the tendency toward alkaline conditions to which second-generation platelet containers (gas permeable polyolefins) are prone.

The blood bags which may be used in this invention are those typical gas permeable alpha polyolefin blood bags commercially available from sources such as Fenwal, Cutter, Baxter-Travenol, etc. No further description of such bags need be given herein as they are well known in the art. Generally these bags are used for storage of donor platelet concentrate and have about 50-60 ml volume capacity.

The compound which is added to provide the necessary stabilizing effect on pH is a non-harmful, non-toxic lactic acid stimulator. Examples of lactic acid stimulators are 2,5-anhydro-D-mannitol, 2,5-anhydro-D-glucitol, D-fructose, D-xylitol, Dglucitol (Sorbitol), phenformin, dithiazanine iodide, methanol, ethanol, salicylate and streptozotocin any of these which are non-toxic or non-harmful may be used.

The most strongly preferred compound is 2,5-anhydro-D-mannitol. This compound, when added, will maintain the pH below about 7.44 and typically within the preferred range of about 7.2 to about 7.44. The important fact in terms of the amount to be added is an amount sufficient to maintain the pH within the range at which blood platelets survive best, namely those pH ranges earlier expressed. For a typical capacity blood bag this amounts to from about 0.mg/bag to about 1000 mg/bag, or practically from about 1 mg to about 500 mg per bag, and most preferred from about 2 mg to about 200 mg per bag.

When the most preferred lactic acid stimulator 2,5-anhydro-D-mannitol is used, the survival rate of the stored platelets is dramatically increased in comparison with the discard rate when transfusions occur without the storage additive.

While applicant does not wish to be bound by any theory, it is believed that the present invention works because the additives of the present invention function as a stimulator for an enzyme which is rate limiting in the production of lactic acid, namely pyruvate kinase and it also inhibits an enzyme fructose bisphosphatase and blocks synthesis of new glucose. Importantly, this compound has an LD50 equal to glucose and is therefore absolutely non-harmful to blood, or to the transfusion recipient.

The following examples are offered to further illustrate, but not limit, the process and product of the present invention.

EXAMPLES

Healthy, volunteer donors (n=40) were bled (450 ml) into polyolefin blood storage bags (CLX-7, Cutter Laboratories, Berkely, CA) containing CPD Adenine-1 (63 ml). Donors were selected and phlebotomized according to well known and published procedures of the American Association of Blood Banks.

The protocol used to prepare the platelet concentrates was as follows: After storage for 1-2 hours at 20°-24° C. the units of whole blood were placed in a temperature-regulated centrifuge (Beckman J-6M) set at 22° C. and spun at 2,500 rpm (1778 g) for 3 minutes. The resulting platelet-rich plasma was then spun at 4,200 rpm (5018 g) for 5 minutes. All but 52 ±2 ml of the supernatent platelet-poor plasma was expressed from the bag and, after 60 minutes of undisturbed storage at 20°-24° C., the platelet pellet was re-suspended by gentle trituration and rotation of the storage bag. The platelet concentrates (PCs) thus obtained were stored at 20°-24° C. with 6 rpm circular agitation. After 8 hours of agitation the platelet count was determined and adjusted to $5.5 \times 10^{10}$ platelets/bag by withdrawing the appropriate amount of PCs and replacing it with autologous plasma. In all of these and subsequent sampling and treatment manipulations PCs were entered aseptically.

Platelet counts were determined by particle counting of PC alignots (500 ml) that had been diluted 1:10 in phosphate buffered saline, pH 7.4. Lactate was measured spectrophotometrically at 340 nm from PC alignots (1 ml) as NADH generated from excess lactate dehydrogenase and NAD . (ACA Chemical Analyzer, Dupont Instruments, Wilmington, DL) Measurements of pH were made from PC alignots (1 ml) that were stored in a capped plastic tube.

D-mannitol was obtained commercially (Pfanstiehl Laboratories, Waukegan, IL). 2,5-anhydro-D-mannitol was prepared by deamination and reduction of D-glucosamine according to a known procedure of Bera, D. C., Foster, A. B. and Stacey, N., J. Chem. Soc. (1956) p. 4531-4541. The fructose 6-phosphate site of phosphofructokinase. J. Biol. Chem. (1974) 249:5749-5754.

Total lactate content was measured in two experiments, each using a different control. A total of 40 platelet concentrates were studied, 20 in each experiment. In the first experiment, the study group (Group I) was composed of 10 platelet concentrates (PC) that each received 10 mg of 2,5-anhydro-D-mannitol dissolved in autologous plasma (1 ml) on Day 0. The control group (Group II) was composed of 10 PCs that each received 1 ml of autologous plasma on Day 0. Both groups were sampled for lactate on Day 0, just prior to injection of the additive or control, then on Days 6, 8 and 17.

In the second experiment, the study group (Group III) was composed of 10 PCs that each received 10 mg of 2,5-anhydro-D-mannitol dissolved in autologous plasma (1 ml). The control group (Group IV) was composed of 10 PCs that each received 10 mg of D-mannitol dissolved in autologous plasma (1 ml) on Day 0. Both groups were sampled for lactate and pH on Day 0, just prior to additive or control, then on Days 6, 7, 8 and 17 for lactate and Days 2 and 7 for pH.

The effect of 2,5-anhydro-D-mannitol on the total lactate content of stored platelet concentrates was compared to two controls. In FIG. 1, the effect of 2,5-anhydro-D-mannitol is compared to a sham treatment (autologous plasma) control and in FIG. 2 to a D-mannitol control. In both experiments, lactate production during storage was significantly increased for the means of the 2,5-anhydro-D-mannitol treated Groups I and III when compared to the control Groups II and IV as illustrated in Table I. On all days studied, the 2,5-anhydro-D-mannitol-stimulated platelet concentrates produced between 38% and 48% more lactate than controls.

In FIG. 3, the effect of 2,5-anhydro-D-mannitol on the platelet concentrate pH was compared to a D-mannitol control. On both days 2 and 7, the pH of the 2,5-anhydro-D-mannitol treated platelet concentrates were significantly lower than the control. Even by Day 7 the pH of the 2,5-anhydro-D-mannitol treated group had not gone above 7.5.

TABLE 1

The Effect of 2,5-anhydro-D-mannitol and Control Treatments on the Change in Lactate Production and pH of Stored Platelet Concentrates

| Group Label and Size | Treatment | Increase in Lactate Production ($umole/10^{10}plt$) Day 6 | Day 7 | Day 8 | Day 17 | Increase in pH Day 2 | Day 7 |
|---|---|---|---|---|---|---|---|
| I(n = 10) | 2,4-anhydro-D-mannitol | 103 ± 5 | | 115 ± 7 | 161 ± 14 | | |
| II(n = 10) | None | 75 ± 8 | | 86 ± 10 | 113 ± 16 | | |
| III(n = 10) | 2,5-anhydro-D-mannitol | 105 ± 11 | 110 ± 11 | 115 ± 11 | 161 ± 17 | 0.18 ± 0.06 | 0.23 ± 0.007 |
| IV(n = 10) | D-mannitol | 70 ± 6 | 75 ± 7 | 80 ± 8 | 104 ± 13 | 0.26 ± 0.03 | 0.46 ± 0.009 |
| I + III (n = 20) | 2,5-anhydro-D-mannitol | 104 ± 6 | | 115 ± 6 | 161 ± 11 | | |
| II + IV (n = 20) | None or D-mannitol | 73 ± 5 | | 83 ± 6 | 109 ± 10 | | |

It can be seen that 2,5-anhydro-D-mannitol is an effective stimulator of lactic acid production. It can also be seen that the acidogenic effect of 2,5-anhydro-D-mannitol can be used to counteract the "respiratory alkalosis" of modern platelet storage containers so as to hold in vitro pH to a stabilized desirable level less than 7.5 and in most cases less than 7.44. Finally, as demonstrated by Table 1, and FIGS. 1 through 3, the objects of the invention are achieved by the addition of 2,5-anhydro-D-mannitol or non-toxic derivatives thereof.

What is claimed is:

1. A method of controlling pH during storage of blood platelets in gas permeable blood storage bags which allow excessive $CO_2$ diffusion causing an increase in alkalinity, said method comprising: placing blood platelets and a small but pH stabilizing amount of 2,5 anhydromannitol in a sealable gas permeable storage bag; and sealing said bag.

2. The method of claim 1 wherein said bag is a polyolefin blood storage bag.

3. A method of controlling pH in stored gas permeable blood bags which allow excessive $CO_2$ diffusion causing an increase in alkalinity, containing blood cells and platelets, said method comprising: adding to said bag a small but pH stabilizing effective amount of 2,5 anhydro-D-mannitol.

4. The method of claim 3 wherein the amount of 2,5-anhydro-D-mannitol is sufficient to maintain the pH below 7.44.

5. The method of claim 4 wherein the amount of 2,5-anhydro-D-mannitol is sufficient to maintain the pH within the range of from about 7.2 to about 7.44.

6. The method of claim 4 wherein the amount of 2,5-anhydro-D-mannitol is from about 0.1 to about 1000 mg/bag.

7. The method of claim 4 wherein the amount of 2,5-anhydro-D-mannitol is from about 1 to 500 mg/bag.

8. The method of claim 7 wherein the amount of 2,5-anhydro-D-mannitol is from about 2.0 to about 200/mg/bag.

9. A gas permeable bag of blood or blood components containing a small but pH stabilizing effective amount of 2,5-anhydro-D-mannitol.

* * * * *